United States Patent [19]

Joslin et al.

[11] 4,353,868
[45] Oct. 12, 1982

[54] SPECIMEN COLLECTING DEVICE

[75] Inventors: Joel A. Joslin, Sunset Hills; Marshall T. Dennison, Creve Coeur, both of Mo.

[73] Assignee: Sherwood Medical Industries Inc., St. Louis, Mo.

[21] Appl. No.: 268,217

[22] Filed: May 29, 1981

[51] Int. Cl.³ .................... B01L 11/00; C12M 1/30
[52] U.S. Cl. .................... 422/101; 128/759; 422/102; 435/295
[58] Field of Search ............... 422/56, 58, 99, 101, 422/102; 128/749, 759; 435/287, 292, 295, 294, 311

[56] References Cited

U.S. PATENT DOCUMENTS

| | | | |
|---|---|---|---|
| 2,835,246 | 5/1958 | Boettger | 128/2 |
| 3,163,160 | 12/1964 | Cohen | 128/2 |
| 3,308,039 | 3/1967 | Nelson | 195/140 |
| 3,450,129 | 6/1969 | Avery et al. | 128/2 |
| 3,579,303 | 5/1971 | Pickering | 23/230 |
| 3,640,268 | 2/1972 | Davis | 128/2 B |
| 3,674,007 | 7/1972 | Freis | 128/2 |
| 3,776,220 | 12/1973 | Monaghan | 128/2 W |
| 3,783,106 | 1/1974 | Henshilwood | 195/139 |
| 3,835,834 | 9/1974 | Brown et al. | 128/2 W |
| 3,890,204 | 6/1975 | Avery | 195/139 |
| 3,913,564 | 10/1975 | Freshley | 128/2 W |
| 3,966,558 | 6/1976 | Calva-Pellicer | 195/139 |
| 4,014,746 | 3/1977 | Greenspan | 195/103.5 R |
| 4,014,748 | 3/1977 | Spinner et al. | 195/127 |
| 4,023,559 | 5/1977 | Gaskell | 128/2 W |
| 4,136,680 | 1/1979 | Southworth | 128/213 |
| 4,150,950 | 4/1979 | Takeguchi et al. | 23/230 B |
| 4,175,008 | 11/1979 | White | 435/295 |
| 4,184,483 | 1/1980 | Greenspan | 128/759 |
| 4,196,167 | 4/1980 | Olsen | 422/61 |
| 4,223,093 | 9/1980 | Newman et al. | 435/295 |

Primary Examiner—Michael S. Marcus
Attorney, Agent, or Firm—Stanley N. Garber; William R. O'Meara

[57] ABSTRACT

A specimen collecting and transporting device is provided which includes a container, a swab in the container connected to a closure cap closing one end of the container, and a reservoir attached to the other end of the container and containing a liquid culture-sustaining medium sealed in a chamber of the reservoir. The bottom end of the container has an opening covered by an absorbent pad and which is in contact with the swab tip. The container has a projection which when moved relatively toward the reservoir, pierces the chamber seal to allow the medium to flow through the opening to the pad and swab tip.

13 Claims, 3 Drawing Figures

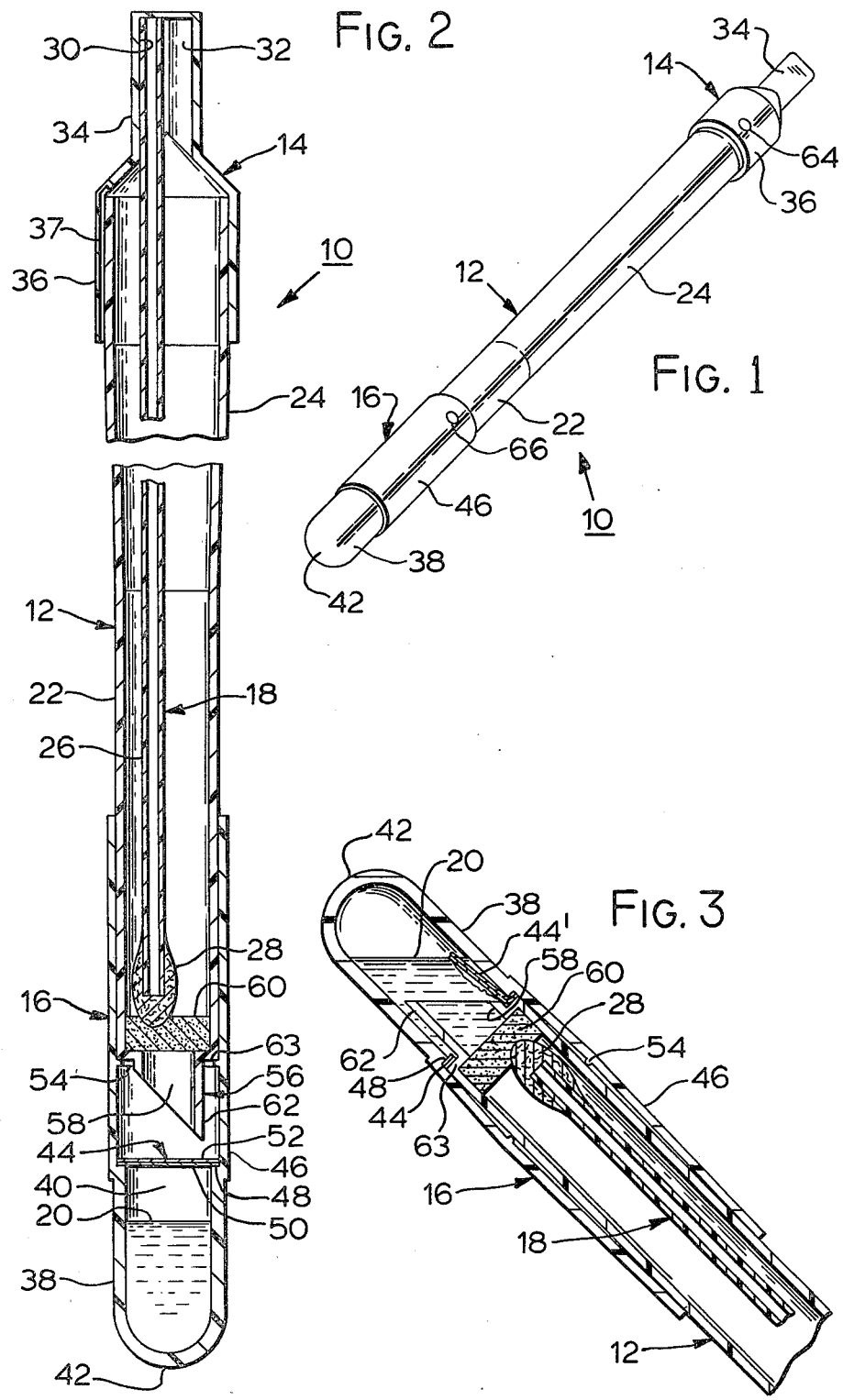

SPECIMEN COLLECTING DEVICE

DESCRIPTION

1. Technical Field

This invention relates to specimen collecting devices and more particularly to specimen collecting devices which have a specimen preserving medium.

2. Background Art

Specimen collection devices generally include a container having a removable swab for obtaining a specimen, such as a culture from a patient's body, for example, from the nose, throat or ear. The container may have a specimen or culture sustaining or preserving medium in a sealed reservoir so that after a culture is taken, the swab is returned to the container and the reservoir opened to allow the medium to contact the swab. The swab may then be transported in the container to the laboratory where the specimen is subjected to clinical analysis.

There are some problems associated with certain collection devices. In some cases, the specimen carrying swab tip is used to force open a chamber containing the culture medium, or the swab tip is held submerged in a quantity of liquid medium. In such cases, there is a significant chance that considerable portions of the specimen will be removed from the swab tip while in the container. Also, the sample may be substantially diluted or modified from its natural state before reaching the laboratory. In some cases, a glass ampule must be manually broken to release the medium. Also, some proposed devices are relatively complicated to use and expensive to make.

DISCLOSURE OF THE INVENTION

It is therefore an object of the present invention to provide an improved specimen collecting and transporting device which is simple and effective in operation; relatively economical to manufacture; and overcomes one or more of the above problems.

In accordance with one aspect of the invention a specimen collecting and transporting device is provided that includes a container having closure means at one end, a reservoir at the opposite end, a specimen sustaining medium in the reservoir, and a swab in the container which is removable for collecting a specimen and returnable for transporting in the container. A seal is provided which normally closes the reservoir, and means for opening the seal and connecting the swab in fluid communication with the medium including means for engaging and breaking the seal in response to relative movement between the container and the reservoir are provided.

These, as well as other objects and advantages of the invention will be apparent from the following detailed description and accompanying drawings.

BRIEF DESCRIPTION OF THE DRAWINGS

FIG. 1 is a perspective view of a specimen collecting and transporting device in accordance with a preferred embodiment of the invention;

FIG. 2 is an enlarged elevational cross-sectional view of device of FIG. 1; and

FIG. 3 is a cross-sectional view of the lower end portion of the device of FIG. 1 but after the seal closing the reservoir chamber has been broken.

DETAILED DESCRIPTION OF THE INVENTION

Referring now to the drawing and particularly to FIGS. 1 and 2, there is shown for illustration a specimen collecting and transporting device 10. Device 10 includes a container or sleeve 12, a closure 14, shown as a removable end cap closing one end of container 12, a reservoir 16 connected to the opposite end of the container, and a swab 18 disposed within the container. The reservoir 16 contains a quantity of a liquid specimen preserving or sustaining medium 20.

Container 12 is shown having a cylindrical lower end portion 22 which receives the reservoir 16, and an outwardly tapering upper end portion 24 integrally connected to portion 22 and which receives the cap 14. The inner diameter of sleeve portion 24 increases to a maximum at the upper open end to facilitate insertion of the swab 18 into the container.

The swab 18 has a rod 26, for example a stick of wood or plastic, and an absorbent swab tip 28 secured, such as by a suitable adhesive, to the bottom end of rod 26. The upper end of rod 26 is frictionally received and held in a bore or socket 30 formed on the inside of cap 14 and extending parallel to the longitudinal axis of the container. Another similar bore or socket 32 adjacent bore 30 is provided so that a second swab (not shown) may be disposed in container 12 if desired. These bores are formed in an upper tubular end portion 34 of cap 14. End portion 34 is integrally connected to a cylindrical portion 36 of greater diameter than portion 34 and which telescopingly receives the upper end portion of container 12. The cap 14 is preferably sized so that it frictionally engages the container 12 and remains in the position in which it is placed on the container. The cap 14 is also provided with an air vent passage 37 which allows air in the container to escape to atmosphere when the device 10 is actuated, as will be discussed hereafter.

When the cap 14 is removed from the container 12 the swab 18 is removed with it. The swab 18 and cap 14 therefore stay together so that the cap 14 can be used as a handle for the swab. The cap 14 facilitates removal of the swab from the container and the return of the swab to the container after a specimen or culture has been obtained by the swab tip 28.

The reservoir 16 includes a lower reservoir portion 38 having a generally cylindrical reservoir chamber 40 closed at the bottom by an integral end wall 42 of the reservoir. The chamber 40 is sealingly closed at the top by a breakable or pierceable seal 44. The reservoir also includes a cylindrical portion or sleeve 46 integrally connected to and extending upwardly from the lower reservoir portion 38. At the juncture of the chamber 40 and sleeve 46 there is an internal annular land 48 on which the seal 44 is disposed. The seal 44 preferably includes a plastic layer 50, such as a layer of polypropylene adhesively flatwise connected to a gas barrier layer 52. The layer 52 may be a metal foil layer, for example, a layer of aluminum foil. By making the reservoir of a plastic compatible with that of the layer 50, the layer 50 can be conveniently induction welded to the land 48 to sealingly close the reservoir chamber 40. For example, where the body of the reservoir 16 is made of polypropylene and the plastic layer 50 is of polypropylene, good induction welding is obtained. In some cases, the seal may be adhesively secured in place, if desired.

The sleeve 46 of the reservoir telescopingly receives the lower end portion 22 of the container 12. Preferably, the sleeve 46 frictionally engages the container but permits relative longitudinal sliding movement between the container 12 and reservoir 16. A stop, shown in the form of an annular abutment 54 on the inner sidewall of the sleeve 46 normally serves as a stop to limit the movement of the container 12 a predetermined distant into the reservoir 16 during assembling of these parts and until the device 10 is put to use, as will be discussed hereafter. Such a stop abutment may be disposed on the outer wall of the container just above the upper end of the sleeve 46 in some cases.

The lower end of the container 12 is provided with a radially inwardly extending bottom end wall 56 having an opening or passage 58 extending through it. A liquid transfer member 60, which may be a quantity of absorbent material, and which is shown as an absorbent pad 60, is disposed within the container 12 against the inside surface of bottom wall 56 closing or covering the opening 58. The parts are dimensioned such that when the cap 14 is closing the upper end of the container 12, the swab tip 28 is held by the cap in good contact engagement with the absorbent pad 60.

The device 10 is provided with a seal breaking member shown for illustration as including a longitudinally extending projection 62 integrally connected to the bottom wall 56 of the container and extending downwardly toward seal 44. The projection 62 is in the form of a tube formed or cut at an angle of about 45° to the longitudinal axis of the container to provide a relatively sharp and pointed member for breaking and piercing the seal 44. Surrounding the projection 62 is an annular shoulder 63 shown in engagement with stop 54 to locate the container 12 with respect to the reservoir 16.

The device 10 may be stored and shipped in the condition shown in FIG. 1 or it may be further packaged such by being placed in a paper and/or plastic bag, or the like.

The cap 14 and the reservoir 16 are preferably spot welded to the container 12 such as at 64 and 66. If these welds are not broken, that fact will indicate to the user that the device 10 had not previously been opened or used.

In use, the cap 14 is rotated relative to container 12 to break weld 64, and then the cap is pulled off of the container. The swab 18 attached to the cap can then be used to obtain a specimen or culture on the swab tip 28. The swab may be returned through the enlarged open end of the container 12 essentially to its original position, that is, the position shown in FIG. 2. The specimen containing tip 28 is disposed against the absorbent pad 60 after the cap 14 is returned to close the upper end of the container.

With the swab 18 and cap 14 back in place, such as shown in FIG. 2, the device 10 is actuated to break the seal 44 and place the pad 60 and swab tip 28 in fluid communication with the specimen preserving medium 20 in reservoir chamber 40. This is accomplished by moving the container 12 and reservoir 16 relative to each so as to effect breaking or piercing of the seal 44 by the seal piercing projection 62.

The seal 44 may be easily and simply broken by projection 62 by holding the container 12 in one hand and striking the bottom end wall 42 on some surface, such as a table top or the like, to thereby break weld 66 and axially or longitudinally move the container 12 relative to the reservoir 12 so that the projection 62 pierces the seal 44 as shown in FIG. 3. During this movement air in the container is allowed to escape through the vent passage 37 in cap 14. The container 12 is preferably moved longitudinally until the annular shoulder 63 of end wall 56 engages peripheral portions of the seal 44 remaining on land 48, as in FIG. 3. A torn portion of the seal 44 is indicated at 44. This places the specimen or culture preserving medium 20 in fluid communication with the passage 58, absorbent pad 60, and the swab tip 28. By inverting the device 10 or positioning the bottom end wall 42 above the container 12, such as by tilting the device as illustrated in FIG. 3, the liquid medium 20 will flow into passage 58 and into contact with absorbent pad 60 which closes or covers passage 58 but which allows controlled or metered flow of the medium through it to the specimen carrying swab tip 28. The device 10 may be inverted or tilted so that the medium flows into the pad 60 for a brief time, for example, a minute or several minutes, depending upon the medium and absorbent materials used, to allow the medium to be absorbed by tip 28. Then the device 10 can be stored or transported in an upright position (FIG. 2). In some cases where it is desired to keep the culture for a relatively longer time, the device 10 may be maintained in an inverted or tilted position for a considerably longer period of time or until it is clinically tested.

If desired, the container and reservoir 16 may be grasped in the hands, rotated relative to each other to break the weld 66, and moved toward each other to move the projection 62 through the seal 44.

The container 12 and reservoir 16 are each constructed of a material which will allow relative movement between them to cause the projection 62 to engage and break or pierce the seal 44. Preferably, they are made of a relatively rigid or semi-rigid plastic such as polypropylene, polyethylene or other plastic. The cap may also be made of a similar plastic. The container 12 and/or reservoir are made flexible enough to permit the lower end of the container to move toward the seal 44 and past the annular stop 54, as is shown in FIG. 3.

After the device is actuated to the condition shown in FIG. 3, the annular shoulder 63 tends to prevent the medium 20 from flowing between the container and reservoir. Also, the annular stop 54 tightly frictionally engages the outer surface of container 12 to provide an additional annular fluid seal between the container 12 and reservoir 16. In this way, even if medium would flow between the reservoir and container members, it would be stopped at the stop 54 so that liquid medium 20 could not flow out of the device 10. This sealing effect would also occur if the annular stop was placed on the outer surface of the container where it would engage the inner surface of sleeve 46.

Since the specimen carrying swab is continuously held in contact with the pad 60, such as by cap 14, the swab tip 28 will remain wet or soaked by the medium so that it can be transported in the closed container 12 to a laboratory for clinical or microscopic analysis. The medium will preserve the collected specimen or culture for an extended period of time depending on design, so that accurate test results can be obtained in the laboratory.

The absorbent swab tip 28 and the absorbent pad 60 may be formed of any suitable absorbent material. The tip 28 may be formed, for example, of polyester fibers. The pad 60 may be formed, for example, of suitable fibers such as rayon fibers or sponge-like material, such as a foam-like urethane material.

Where the liquid transfer and fluid flow metering member 60 is used, the specimen-carrying swab tip 28 is returned to its original position above the reservoir with the specimen substantially undisturbed. The specimen is substantially in its natural state or state in which it was obtained, and it is substantially not modified or diluted as in some cases where the swab tip is placed in a certain liquid or medium. In this way, the swab can be used to apply the specimen to a microscopic slide or to a dish for incubation.

In some cases, the absorbent member may not be employed in device 10, however, it is a preferred element, especially when the medium has a low viscosity or is very thin or fluid. When the medium is very fluid, the metering effect of member 60 prevents the fluid and portions of the specimen from getting on the swab handle or stick 26 and the cap 14, and thus prevents contamination of these parts.

Various well known liquid culture-sustaining mediums are usable in device 10. The particular culture medium used is chosen on the basis of the particular type of culture to be preserved. A liquid culture medium such as Stuart's Modified Media, or a liquid culture of bile, blood or egg may be used. Gel-type mediums are also sometimes used.

Where desired, a label with the patient's identification can be applied to the outer surface of the device 10.

As various changes could be made in the above construction without departing from the scope of the invention, it is intended that all matter contained in the above description and apparatus shown in the accompanying drawing shall be interpreted as illustrative and not in a limiting sense.

We claim:

1. A specimen collecting and transporting device comprising a longitudinally extending sleeve container member including a removable cap for selectively closing and opening one end of said container member, a swab in said container member including a rod connected adjacent one end thereof to said cap, and an absorbent tip connected to the opposite end of said rod, the opposite end of said container member having an opening therethrough, and seal piercing means extending from said container member opposite end, fluid flow metering means covering said opening and being in contact with said absorbent tip, a reservoir member having a sleeve receiving an opposite end portion of said container member in longitudinal slidable relation therewith, a reservoir chamber having a closed bottom end, an upper open end, a seal closing said upper open end of said chamber, and a liquid culture-sustaining medium in said chamber, and means including abutment means on one of said members engagable with the other of said members for locating said container member in a position relative to said reservoir member wherein said piercing means is above said seal, said container and reservoir members being relatively slidable to move said piercing means through said seal and connect said opening and absorbent pad in fluid communication with said medium and thereby wet said absorbent tip.

2. The device of claim 1 wherein said members are longitudinally slidable relative to each other.

3. The device of claim 1 wherein said reservoir member is formed of a plastic material, and said seal includes a layer of plastic material which is induction heat bondable to said reservoir plastic material.

4. The device of claim 3 wherein said seal includes a second layer of metal foil.

5. The device of claims 2 or 4 wherein said container and reservoir members are formed of relatively rigid plastic material.

6. The device of claim 1 wherein said reservoir member includes other abutment means limiting movement of said opposite end of said container member relative to said reservoir when said container and reservoir members are relatively moved to effect piercing of said seal by said piercing means.

7. The device of claim 6 wherein said other abutment means includes an annular shoulder at the upper end of said chamber, said seal being secured on said shoulder, and said opposite end of said container member being engageable with said seal after said piercing means has pierced said seal.

8. The device of claim 6 wherein said seal is heat sealed to said other abutment means.

9. The device of claim 1 wherein said abutment means includes an annular rib on said one member frictionally engageable with the surface of the sidewalls of said other member upon relative movement between said container and reservoir members, said abutment means providing a liquid seal between said members.

10. The device of claim 1 wherein said opening is a passage through said seal piercing means.

11. The device of claim 1 wherein said cap includes a sleeve portion which receives said one end of said container member, and a socket for frictionally receiving an end portion of said rod adjacent said one end of said rod.

12. The device of claim 1 wherein said container member includes at least a portion thereof which increases in diameter toward said one end thereof to facilitate reentry of said swab into said container member after obtaining a specimen thereon.

13. The devices of claim 1 wherein said fluid flow metering means is an absorbent member.

* * * * *